United States Patent
Bari et al.

(10) Patent No.: US 11,945,809 B2
(45) Date of Patent: Apr. 2, 2024

(54) ISATIN DERIVATIVES

(71) Applicant: KING SAUD UNIVERSITY, Riyadh (SA)

(72) Inventors: Ahmed Bari, Riyadh (SA); Saeed Ali Syed, Riyadh (SA); Mohammad A. Altamimi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/932,787

(22) Filed: Jul. 19, 2020

(65) Prior Publication Data
US 2023/0357213 A1    Nov. 9, 2023

(51) Int. Cl.
*C07D 409/12* (2006.01)
*A61P 35/00* (2006.01)

(52) U.S. Cl.
CPC ............ *C07D 409/12* (2013.01); *A61P 35/00* (2018.01)

(58) Field of Classification Search
CPC .............................. C07D 409/12; A61P 35/00
See application file for complete search history.

(56) References Cited

U.S. PATENT DOCUMENTS

| 3,632,587 | A | * | 1/1972 | Hollowood | .......... | C07D 209/38 |
| | | | | | | 544/373 |
| 4,780,477 | A | * | 10/1988 | Kobayashi | ................ | A61P 1/04 |
| | | | | | | 514/418 |
| 5,883,113 | A | | 3/1999 | Tang et al. | | |
| 7,662,824 | B2 | | 2/2010 | Leonard et al. | | |
| 8,497,296 | B2 | | 7/2013 | Hassan et al. | | |
| 2006/0009493 | A1 | | 1/2006 | Koenig et al. | | |

FOREIGN PATENT DOCUMENTS

| EP | 2604600 A1 | 6/2013 |
| WO | 2018100484 A1 | 6/2018 |

OTHER PUBLICATIONS

Vine et al., "Cytotoxic and Anticancer Activities of Isatin and Its Derivatives: A Comprehensive Review from 2000-2008," Anti-Cancer Agents In Medicinal Chemistry, 2009, 9, pp. 397-414.
Aboul-Fadl et al. "Anti-tubercular activity of isatin derivatives.," International Journal of Research in Pharmaceutical Sciences, vol. 1, Issue 2, 2010.
Dweedar et al., "Analogue-based design, synthesis and biological evaluation of 3-substituted-(methylenehydrazono) indolin-2-ones as anticancer agents.," European Journal of Medicinal Chemistry, 78, (2014), pp. 275-280.

* cited by examiner

*Primary Examiner* — Sarah Pihonak
(74) *Attorney, Agent, or Firm* — Nath, Goldberg & Meyer; Richard C. Litman

(57) ABSTRACT

A method of treating cancer can include administering one or more of the isatin derivatives to a patient in need thereof. In an embodiment, the cancer is selected from the group consisting of breast cancer, non-small cell lung cancer, renal cancer and melanoma. The isatin derivative is selected from the group consisting of:

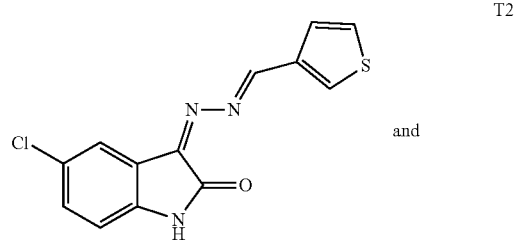

and

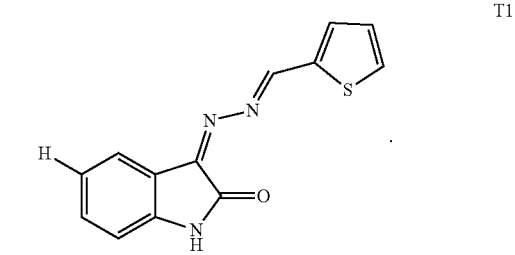

3 Claims, 5 Drawing Sheets

ISATIN DERIVATIVES

BACKGROUND

1. Field

The disclosure of the present patent application relates to isatin derivatives as anticancer agents, and particularly to 1H-indole-2,3-dione derivatives.

2. Description of the Related Art

Cancer is one of the leading causes of death in the world, primarily characterized by a loss of control of cell growth in any cell type. Chemotherapy remains one of the primary modalities for the treatment of cancer. However, the use of available chemotherapeutics is limited mainly due to drug resistance and toxicity. Resistance to chemotherapies and damage due to chemotherapy toxicity limit the use of existing chemotherapeutic drugs. Combinations of chemotherapies are often pursued, as targeting different proteins increases chemotherapeutic efficiency, antagonizes resistance development, and decreases toxicity effects.

1H-indole-2,3-dione or isatin is a heterocyclic natural product found in plants of the genus *Isatis*, and is also present in humans as a metabolic derivative of adrenaline. Isatin is a versatile synthetic intermediate with various pharmacological properties.

Thus, isatin derivatives useful as anticancer agents and methods of treating cancer involving such isatin derivatives solving the aforementioned problems are desired.

SUMMARY

The present disclosure provides an isatin derivative selected from the group consisting of:

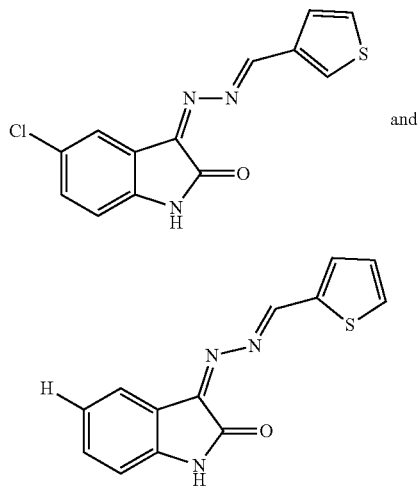

or a pharmaceutically acceptable salt thereof.

A method of treating cancer can include administering one or more of the isatin derivatives to a patient in need thereof. In an embodiment, the cancer is selected from the group consisting of breast cancer, non-small cell lung cancer, renal cancer and melanoma. In an embodiment, the method of treating cancer can include inhibiting the growth of at least one of non-small cancer cells (NCI-H522), renal cancer cells (CAKI-1), and melanoma cells (MDA-MB-435) by administering compound T1 to the patient. In an embodiment, the method of treating cancer can include inhibiting the growth of breast cancer cells (MDA-MB-468) by administering compound T2 to the patient.

Other embodiments include pharmaceutical compositions comprising the isatin derivatives, methods of synthesizing such compounds and pharmaceutical compositions.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

The isatin derivative, according to the present teachings, is a compound selected from T1 and T2, as defined below:

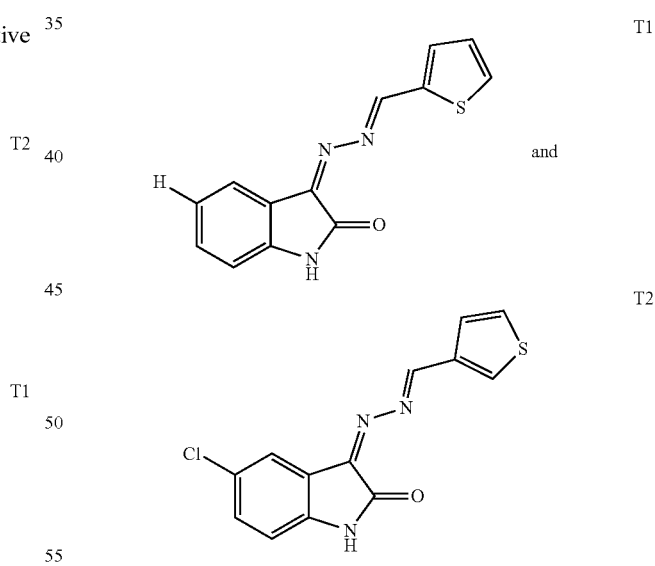

or a pharmaceutically acceptable salt thereof.

In an embodiment, a method of treating cancer can include administering the isatin derivative to a patient in need thereof. In an embodiment, the cancer is at least one of breast cancer, non-small cell lung cancer, renal cancer, and melanoma. In an embodiment, the method of treating cancer can include inhibiting the growth of at least one of non-small cancer cells, renal cancer cells, and melanoma cells by administering compound T1 to the patient. In an embodiment, the non-small cancer cells are from the NCI-H522 cell line. In an embodiment, the renal cancer cells are from the CAKI-1 cell line. In an embodiment, the melanoma cells are from the MDA-MB-435 cell line. In an embodiment, the method of treating cancer can include inhibiting the growth of breast cancer cells by administering compound T2 to the patient. In an embodiment, the breast cancer cells are from the MDA-MB-468 cell line.

In an embodiment, the method can include preparing the isatin derivative and determining an appropriate dosing regimen for administering the isatin derivative. The isatin derivative can be administered pursuant to the dosing regimen.

An embodiment of the present teaching is directed to the following isatin derivative

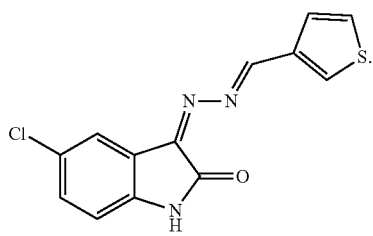

As described in the following Examples, the isatin derivatives can inhibit growth of cancer cells. Accordingly, the methods of treating cancer according to embodiments discussed above may be combined with any existing cancer therapy, including surgery, radiation, additional chemotherapy or immune therapy.

Other embodiments of the present subject matter include a pharmaceutical composition comprising one or more of the isatin derivatives and a pharmaceutically acceptable carrier.

Figure 1:
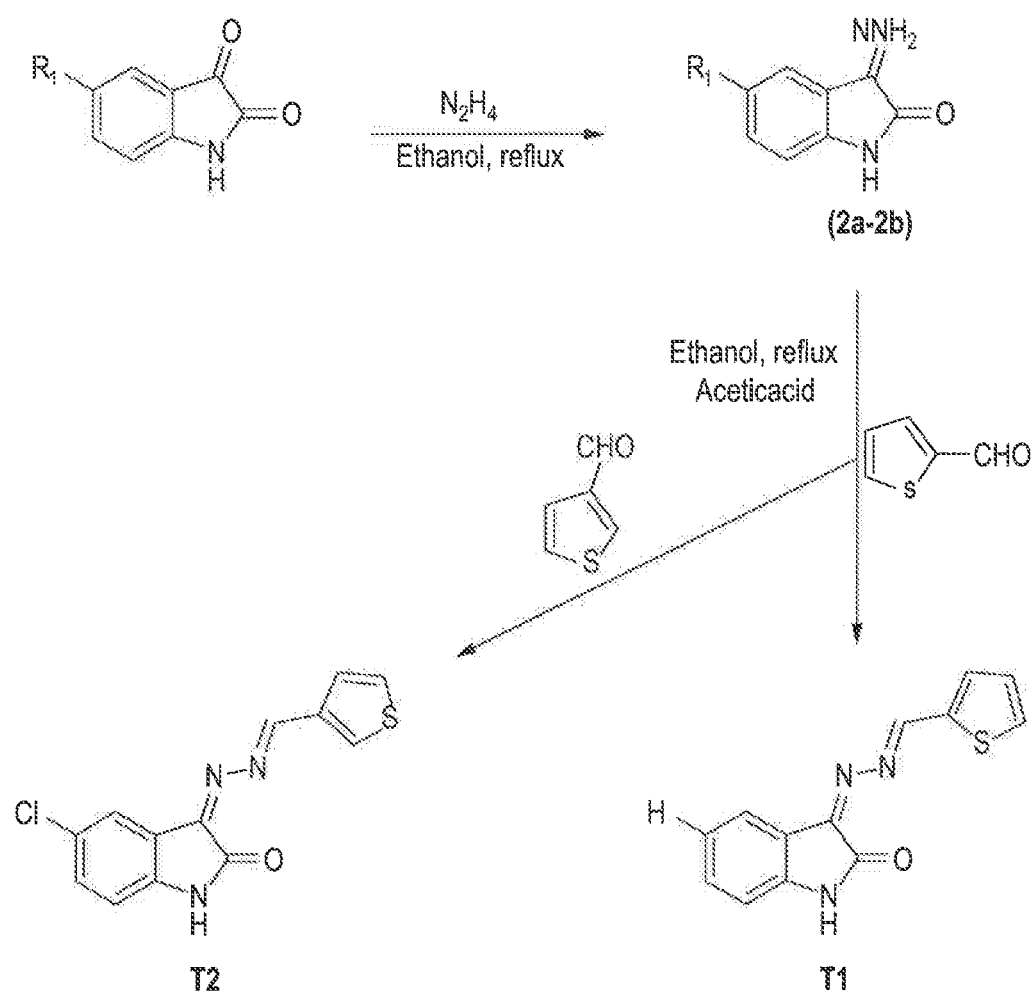
FIG. 1 depicts a synthesis scheme of exemplary compounds 3-((E)-(thiophen-2-ylmethylene) hydrazono) indolin-2-one (T1) and 5-chloro-3-((E)-(thiophen-3-ylmethylene) hydrazono) indolin-2-one (T2).

The isatin derivatives may be synthesized as illustrated in the exemplary reaction scheme shown in FIG. 1. Referring to FIG. 1, compounds T1 and T2 may be synthesized by reacting 3-hydrazonoindolin-2-one 2a with thiophene-2-carboxaldehyde (for compound T1) in a solvent or 5-chloro-3-hydrazonoindolin-2-one 2b with thiophene-3-carboxaldehyde (for compound T2) in a solvent, and a catalytic amount of acetic acid at room temperature. The resulting mixtures may be refluxed and the solvent evaporated to obtain a solid. The solid may be washed and recrystallized to afford the desired isatin derivatives.

Exemplary samples of the isatin derivatives were synthesized, as described in the following examples, and the structures of all of the synthesized compounds were determined by nuclear magnetic resonance (NMR), Fourier transform infrared spectroscopy (FTIR), mass spectroscopy (MS), and elemental analysis.

It should be understood that the amounts of materials for the methods described herein are exemplary, and appropriate scaling of the amounts are encompassed by the present subject matter, as long as the relative ratios of materials are maintained. As used herein, the term "about," when used to modify a numerical value, means within ten percent of that numerical value.

The isatin derivatives can include at least one of 3-((E)-(thiophen-2 ylmethylene) hydrazono) indolin-2-one (T1) and 5-chloro-3-((E)-(thiophen-3-ylmethylene) hydrazono) indolin-2-one (T2), or a pharmaceutically acceptable salt thereof. The anticancer molecules can be used as an active ingredient of pharmaceutical compositions for treating renal cancer, breast cancer, melanoma, and non-small cell lung cancer. The pharmaceutical compositions may include different concentrations of the isatin derivatives. Diluting solvents may include, for example, water, saline or alcohol. The isatin derivatives may be administered in crystal or amorphous forms. The isatin derivatives may be given as liposome formulations.

A pharmaceutically acceptable salt includes hydrochlorides, carbonates, bicarbonates, benzene sulfonate, benzoate, gluconate, mesylate, acetate, phosphate and p-toluene sulfate salts, which are generally prepared by the reaction of free acid with a suitable base. The base may be either organic or inorganic.

The isatin derivatives can be administered by any acceptable route, including oral, intravenous, transdermal, or directly to the region requiring chemotherapy by any chemotherapeutic means. As a further alternative, the isatin derivatives may be administered as liposome formulations. Liposomes are phospholipid-based vesicles which may enclose the isatin derivatives. Liposomes, loaded with the isatin derivatives, can be dispersed in aqueous medium, which may include stabilizers, preservatives and excipients.

It should be understood that the pharmaceutical compositions can include one or more of the isatin derivatives or pharmaceutically equivalent salts thereof. One or more of the isatin derivatives can be mixed with a pharmaceutically acceptable excipient as per acceptable pharmaceutical compounding procedures. Excipients include, but are not limited to, binders, suspending agents, lubricants, flavoring, sweeteners, preservatives, dyes and coatings. In preparation of liquid oral dosage forms, any pharmaceutical carriers may be used, such as water, glycerol, alcohols, preservatives and coloring agents. In solid dosage forms, carriers include, but are not limited to, starches, sugars, granulating agents and binders. Injectable preparations may also be prepared, for which acceptable pharmaceutical carriers include, but are not necessarily limited to alcohol, dimethylsulfoxide (DMSO), and saline. Other potential formulations may include nanoparticle formulations, micellar formulations, biodegradable formulations, and water soluble formulations.

Pharmaceutical compositions for intravenous injections can include sterile water, preservatives, wetting agents, excipients and dispersion agents. Various antibacterial and antifungal agents may be used to prevent microbial growth, including paraben, chlorobutanol, and ethanol. Gelatin may be used for prolonged absorption of the isatin derivatives in the body. For slow release of the isatin derivatives, crystalline or materials with poor water solubility may be used.

The present compositions may be formulated as tablets, pills, capsules, powders, ampules, sterile solutions and auto injector modules, for example, and in various concentrations. The isatin derivatives may be mixed with a pharmaceutically acceptable carrier or excipient appropriate for the formulation. A therapeutically effective dose or an amount of the isatin derivative or pharmaceutical composition may be determined initially according to the nature of the cancer and the organ affected.

The following examples illustrate the present teachings.

EXAMPLES

Example 1

Synthesis of the Isatin Derivatives

Exemplary samples of isatin derivatives T1 and T2 were prepared by the reaction of 2a (1 mmol) and 2b (1 mmol), respectively, in ethanol (50 mL) with thiophene-2-carboxaldehyde (1.1 mmol) and thiophene-3-carboxaldehyde (1.1 mmol), respectively. Addition of a catalytic amount of acetic acid at room temperature facilitated completion of the reaction. Acetic acid as a catalyst enhances the yield of the products. The resulting mixtures were refluxed for 3 hours with stirring. The solvents of the refluxed mixtures were evaporated in vacuo to produce a solid. The solid was washed with cold water several times and recrystallized with ethanol to afford the exemplary samples, characterized as below.

3-((E)-(thiophen-2-ylmethylene)hydrazono)indolin-2-one (labeled as T1): Yield: 82%, M.P. 196-198° C., FTIR (KBr): v=cm$^{-1}$, 1660 (C=N), 1731 (C=O), 3259 (NH). $^1$HNMR (500.133 MHz, DMSO-d$_6$): δ=6.91 (d, 1H, thiophene), 7.07 (t, 1H, Ph), 7.30 (m, 1H, thiophene), 7.41 (t, 1H, thiophene), 7.81 (m, 1H, Ph), 7.98 (m, 1H, Ph), 8.03 (dd, 1H, Ph), 9.93 (s, 1H, CH), 10.86 (s, 1H, NH). $^{13}$C NMR (125.76 MHz, DMSO-d$_6$): δ=111.3, 117.1, 122.7, 129.3, 129.4, 133.6, 134.1, 135.8, 138.9, 145.5, 151.8, 157.6, 165.1.

5-chloro-3-((E)-(thiophen-3-ylmethylene) hydrazono)indolin-2-one (labeled as 72): Yield: 77%, M.P. 230-235° C. (decomposition), FTIR (KBr): v=cm$^{-1}$, 1669 (C=N), 1721 (C=O), 3239 (NH). $^1$HNMR (500.133 MHz, DMSO-d$_6$): δ=6.91 (d, 1H, thiophene), 6.97 (m, 1H, Ph), 7.22 (s, 1H, thiophene), 7.39 (t, 1H, thiophene), 7.95 (m, 1H, Ph), 8.13 (m, 1H, Ph), 9.89 (s, 1H, CH), 10.89 (s, 1H, NH). $^{13}$C NMR (125.76 MHz, DMSO-d$_6$): δ=110.3, 117.4, 122.5, 129.6, 129.4, 137.6, 134.1, 135.5, 138.9, 145.2, 151.8, 157.6, 165.1.

Example 2

Methodology of In Vitro Anticancer Screening

Anticancer activities of the exemplary isatin derivatives were tested by the NIH National Cancer Institutes (NCI) with results summarized in FIGS. 2A-3B. The anticancer activity was tested by NCI, division of cancer treatment and diagnosis, according to the NCI-60 Human Tumor Cell Lines Screen, one-dose screen (https://dtp.cancer.gov/discoverv_development/nci-60/methodology.htm). This screening allows for qualified synthesized chemicals to be subjected to an anticancer test against 60 different cancer cell lines. Briefly, exemplary T1 or T2 was dissolved in DMSO:Glycerol, 9:1, at 4 mmol and kept frozen prior to use. For inoculation, a 96 well microtiter was used for the study of different cell lines. Based on the doubling time for each cell line, the well density varied. The plates were incubated at 37° C., 5% CO$_2$, 95% air and 100% relative humidity for 1 day. The exemplary T1 or T2 or a control were added to the plates at a concentration of 10-M. After 2 more days, the plates were fixed and stained to identify growth inhibition relative to cells without drug treatment. Anti-proliferative activity was determined based on careful analysis of historical DTP screening data. Cell death and net growth inhibition were determined based on a time zero control. A value of 100 indicates no growth inhibition. A value of 40 indicates 60% growth inhibition. A value of 0 indicates no net growth over the course of the experiment. A value of −40 indicates 40% lethality. A value of −100 indicates that all cells are dead.

Figure 2A:
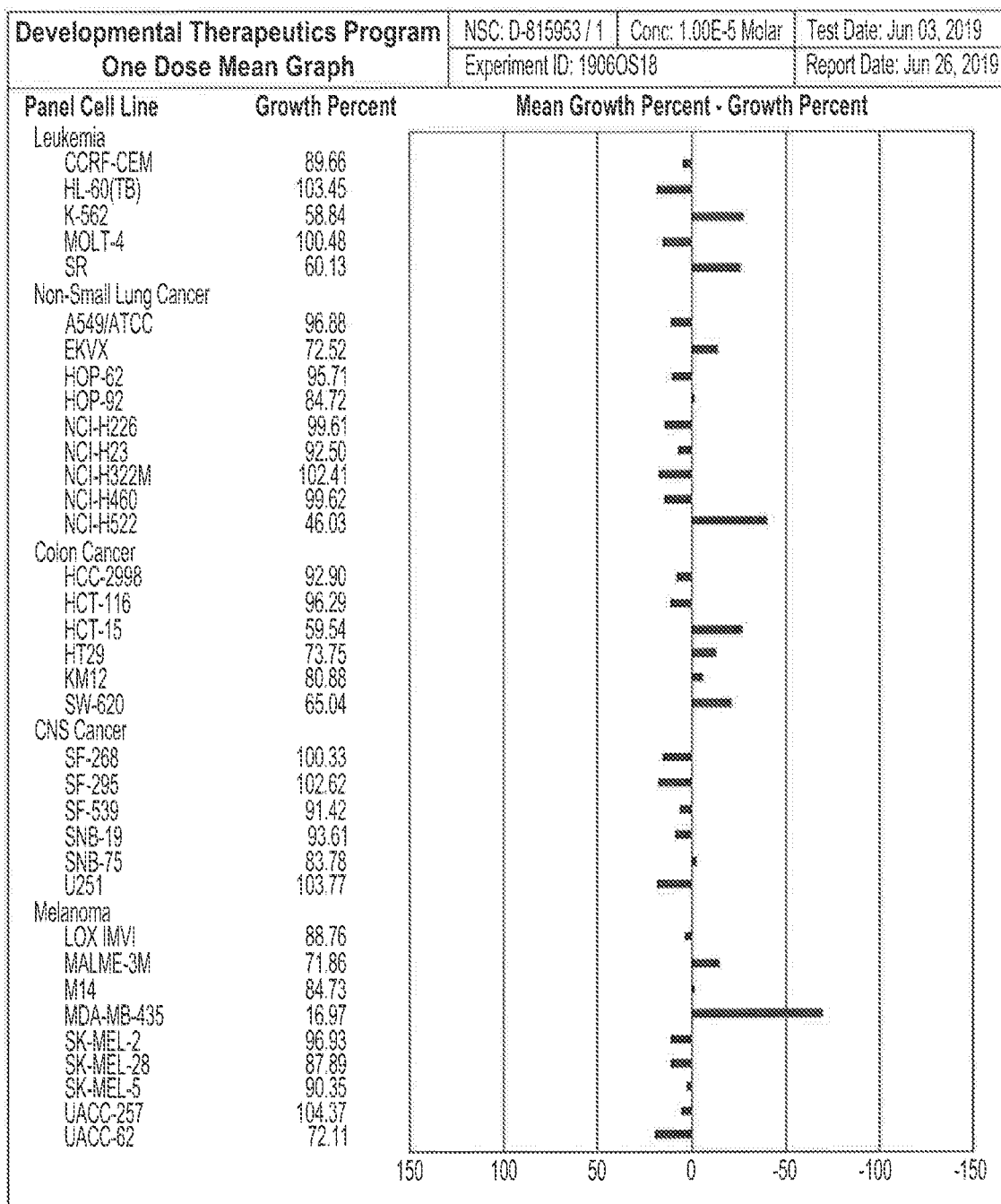
FIGS. 2A-2B provide levels of anticancer activities of the isatin derivative T1 for a diverse range of model cancer cell strains.
Figure 2B:
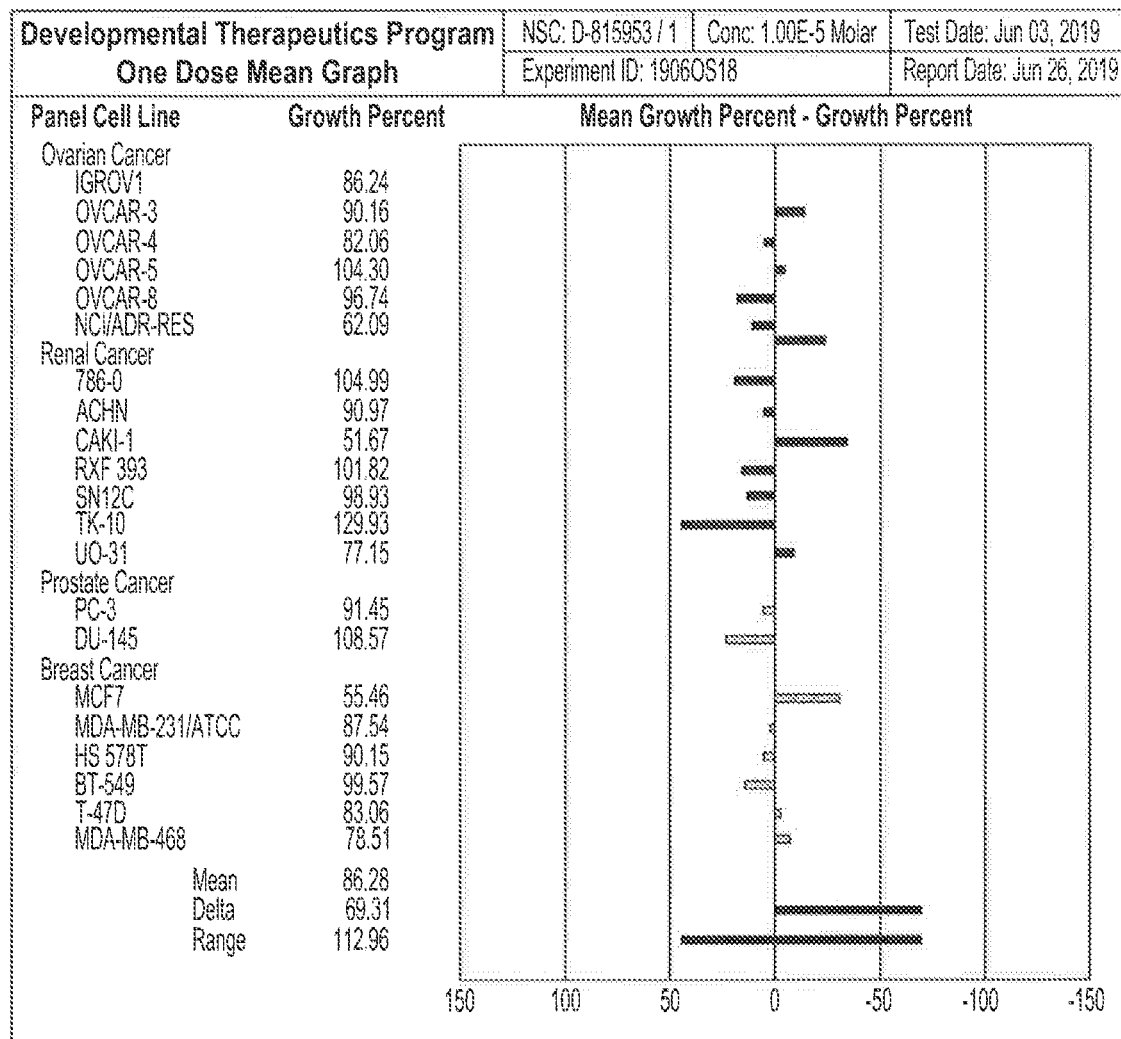

As shown in FIGS. 2A-2B, T1 exhibited a range of anticancer activities against the 60 different cancer cell lines tested. The most significant anticancer activities compared to control were achieved for Non-Small Cell Lung Cancer cells (EKVX) (~54% reduction), Renal Cancer cells (CAKI-1) (~48% reduction) and Melanoma cells (MDA-MB-435) (~83% reduction).

Figure 3A:
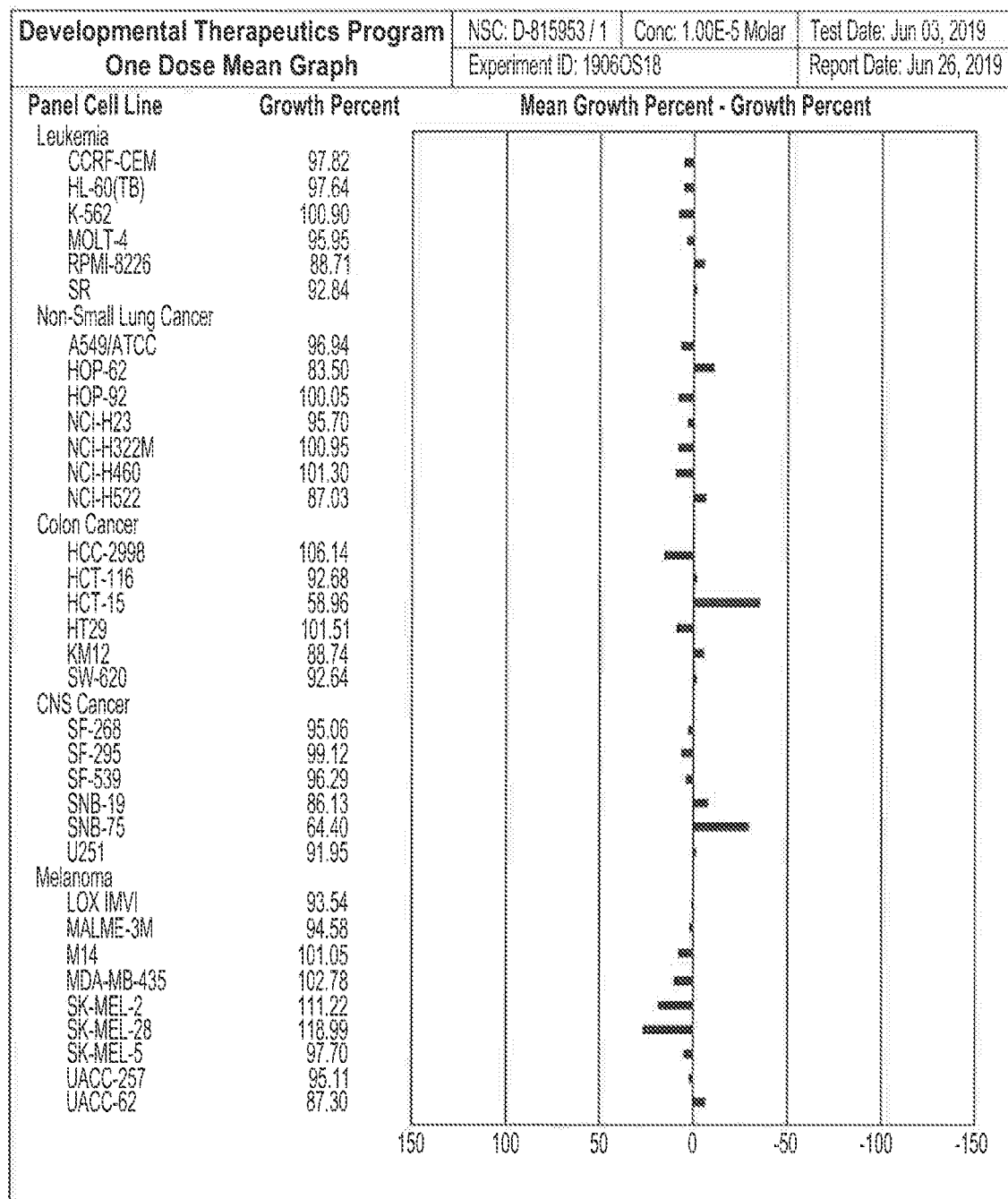
FIGS. 3A-3B provide levels of anticancer activities of the isatin derivative T2 for a diverse range of model cancer cell strains.
Figure 3B:
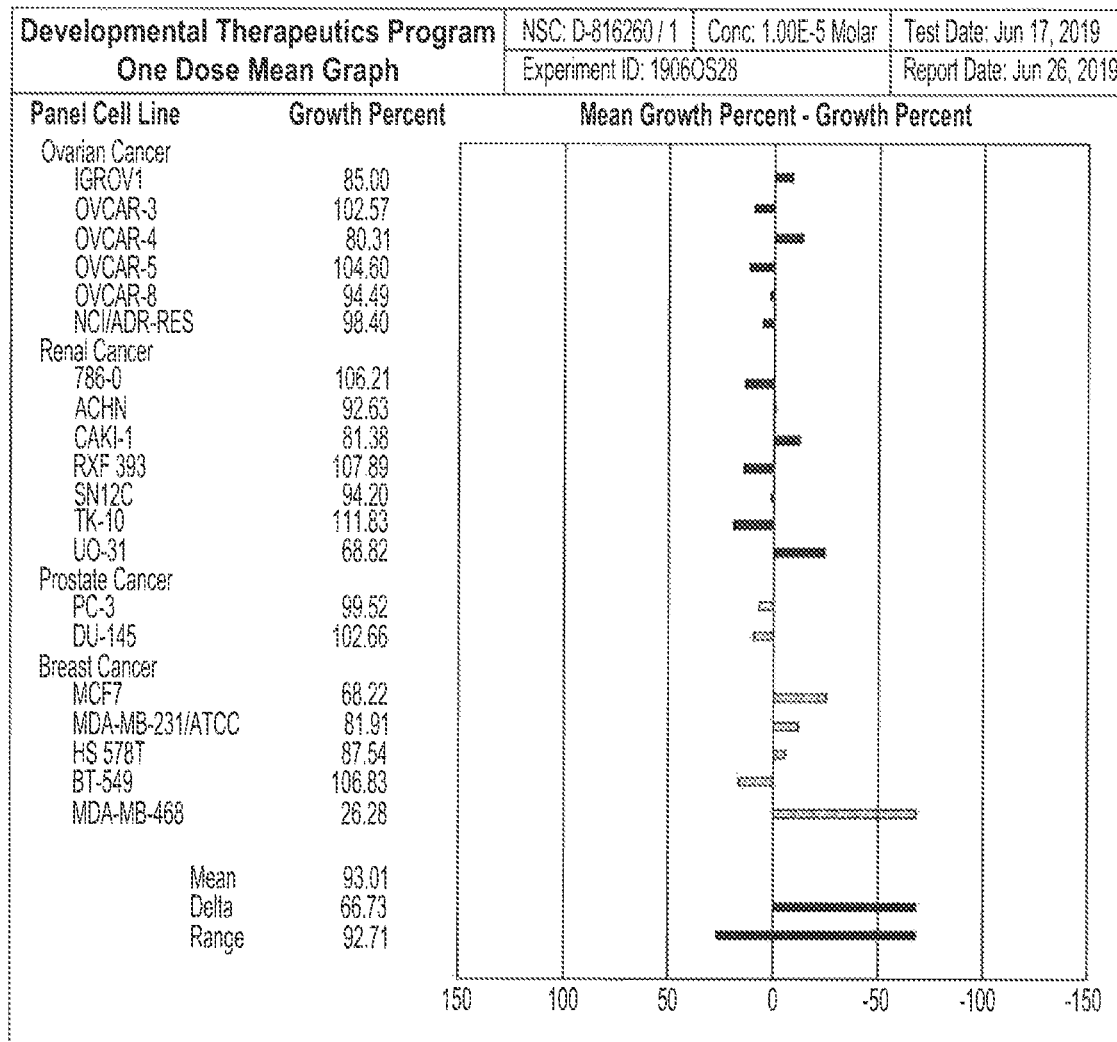

As shown in FIGS. 3A-3B, T2 exhibited a range of anticancer activities against the 60 different cancer cell lines tested. The most significant anticancer activities compared to control were achieved for Breast Cancer cells (MDA-MB-468) (~73% reduction).

Each of T1 and T2 showed additional activities against other cell types, as depicted in FIGS. 2A-3B.

It is to be understood that the isatin derivatives and related compositions and methods are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An isatin derivative having the formula:

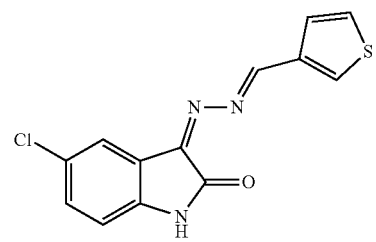

T2 or a pharmaceutically acceptable salt thereof, so as to have anticancer activity against breast cancer cells (MDA-MB-468).

2. A method of synthesizing an isatin derivative, the isatin derivative having the formula:

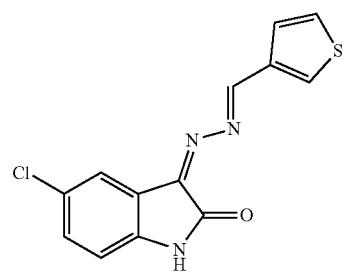

T2 wherein the method comprises the steps of:
dissolving a precursor of an isatin derivative in ethanol to form a solution, wherein the precursor is 5-chloro-3-hydrazonoindolin-2-one;
mixing the solution with thiophene-3-carboxaldehyde;
adding a catalytic amount of acetic acid to form a reaction mixture;
refluxing the reaction mixture; and
evaporating a solvent in the mixture to produce a solid comprising the isatin derivative.

3. The method of claim 2, further comprising the steps of:
washing the solid with water and recrystallizing the washed solid to isolate the isatin derivative.

* * * * *